(12) United States Patent
Fu et al.

(10) Patent No.: US 8,663,125 B2
(45) Date of Patent: *Mar. 4, 2014

(54) DUAL PATH NOISE DETECTION AND ISOLATION FOR ACOUSTIC AMBULATORY RESPIRATION MONITORING SYSTEM

(75) Inventors: Yongji Fu, Vancouver, WA (US); Yungkai Kyle Lai, Aliso Viejo, CA (US); Bryan Severt Hallberg, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 355 days.

This patent is subject to a terminal disclaimer.

(21) Appl. No.: 13/065,816

(22) Filed: Mar. 30, 2011

(65) Prior Publication Data

US 2012/0253215 A1 Oct. 4, 2012

(51) Int. Cl.
*A61B 5/08* (2006.01)

(52) U.S. Cl.
USPC .......................................................... 600/529

(58) Field of Classification Search
USPC ................................................. 600/529–543
See application file for complete search history.

(56) References Cited

U.S. PATENT DOCUMENTS

| | | | | |
|---|---|---|---|---|
| 4,306,567 A * | 12/1981 | Krasner | ...................... | 600/484 |
| 5,143,078 A * | 9/1992 | Mather et al. | ................... | 600/529 |
| 6,654,623 B1 * | 11/2003 | Kastle | ........................... | 600/336 |
| 7,174,206 B2 | 2/2007 | Frei et al. | ....................... | 600/544 |
| 726,765 A1 | 9/2007 | Coyle et al. | | |
| 740,480 A1 | 7/2008 | Seijko et al. | | |
| 7,412,281 B2 | 8/2008 | Shen et al. | ..................... | 600/509 |
| 746,090 A1 | 12/2008 | Kettunen | | |
| 750,264 A1 | 3/2009 | Farringdon et al. | | |
| 751,504 A1 | 4/2009 | Welch | | |
| 7,515,054 B2 | 4/2009 | Torch | | |
| 7,761,128 B2 | 7/2010 | Al-Ali et al. | ................... | 600/323 |
| 7,762,953 B2 | 7/2010 | Derchak et al. | ............... | 600/300 |
| 7,813,780 B2 | 10/2010 | Shah et al. | ..................... | 600/345 |
| 7,818,049 B2 | 10/2010 | Halperin et al. | .............. | 600/509 |
| 2005/0061315 A1 | 3/2005 | Lee et al. | | |
| 2007/0282212 A1 | 12/2007 | Sierra et al. | | |
| 2010/0255505 A1 | 10/2010 | Xu et al. | | |
| 2011/0054339 A1 * | 3/2011 | Gass et al. | ..................... | 600/529 |
| 2011/0295138 A1 * | 12/2011 | Lai et al. | ........................ | 600/529 |
| 2012/0029298 A1 * | 2/2012 | Fu et al. | ........................... | 600/300 |
| 2012/0071744 A1 * | 3/2012 | Euliano et al. | ................ | 600/382 |
| 2012/0253214 A1 * | 10/2012 | Fu et al. | ......................... | 600/529 |

OTHER PUBLICATIONS

Yongji Fu et al., Signal Quality Classification for an Ambulatory Monitoring System, 32nd Ann. Int'l Conf. IEEE EMBS, Sep. 4, 2010, pp. 174-177.

Yongji Fu et al., Pulmonary Disease Management System with Distributed Wearable Sensors, 31st Ann. Int'l Conf., IEEE EMBS, Sep. 6, 2009, pp. 773-776.

* cited by examiner

*Primary Examiner* — Michael Kahelin
*Assistant Examiner* — Karen Toth
(74) *Attorney, Agent, or Firm* — Scot A. Reader

(57) ABSTRACT

Dual path noise detection and isolation for an acoustic respiration monitoring system detects noise in an acoustic signal recording lung sounds using two discrete noise detection techniques. A first technique detects portions of the signal that exhibit long-term, moderate amplitude noise by analyzing cumulative energy in the signal. A second technique detects portions of the signal that exhibit short-term, high amplitude noise by analyzing peak energy in the signal. Noisy portions of the signal are isolated using the combined results of the dual path detection. A respiration parameter is estimated using the signal without resort to the noisy portions and information based at least in part on the respiration parameter is outputted.

20 Claims, 7 Drawing Sheets

DUAL PATH NOISE DETECTION AND ISOLATION FOR ACOUSTIC AMBULATORY RESPIRATION MONITORING SYSTEM

CROSS-REFERENCE TO RELATED APPLICATION(S)

This application has subject matter related to application Ser. No. 13/065,815 entitled "MULTISTAGE METHOD AND SYSTEM FOR ESTIMATING RESPIRATION PARAMETERS FROM ACOUSTIC SIGNAL," filed Mar. 30, 2011, published as U.S. Patent Application Publication No. 2012/0253214.

BACKGROUND OF THE INVENTION

The present invention relates to physiological monitoring and, more particularly, to noise handling in acoustic ambulatory respiration monitoring.

Ambulatory respiration monitoring can be helpful in maintaining the respiratory health of people as they go about their daily lives. For example, ambulatory respiration monitoring can enable prompt discovery of a problem with the respiratory health of a person who suffers from a chronic pulmonary disease or works in hazardous environment so that the person can obtain timely treatment. Since respiration sound contains vital signs such as respiration rate and heart rate, ambulatory respiration monitoring can also be applied to other fields such as senior monitoring and sleep monitoring.

Ambulatory respiration monitoring often invokes the respiration sound method, sometimes called auscultation. In the respiration sound method, an acoustic transducer mounted on the body of the person being monitored captures and acquires an acoustic signal recording lung sounds. The sound transducer is typically placed over the suprasternal notch or at the lateral neck near the pharynx because lung sounds captured in that region typically have a high signal-to-noise ratio and a high sensitivity to variation in flow. Once the acoustic signal with recorded lung sounds has been generated, respiration phases are identified in the acoustic signal and respiration parameter estimates (e.g., respiration rate, inspiration/expiration ratio) are calculated. Respiration health status information based on respiration parameter estimates may then be outputted locally to the monitored person or remotely to a clinician.

One problem commonly encountered in acoustic ambulatory respiration monitoring is parameter estimation error caused by noise. An acoustic signal that records lung sounds in a mobile environment can be disrupted by several types of noise, such as long-term, moderate amplitude noise introduced by the surrounding environment, or short-term, high amplitude noise introduced by impulse events such as coughing or sneezing. Regardless of the source, noise can result in erroneous estimation of respiration parameters and outputting of erroneous respiration health status information. In turn, reliance on outputted information that is erroneous can have serious adverse consequences on the health of the monitored person. For example, such information can lead the person or his or her clinician to improperly diagnose respiration health status and cause the person to undergo treatment that is not medically indicated or forego treatment that is medically indicated.

Known approaches to combating noise-induced parameter estimation error, such as using a reference microphone to measure environmental noise and attempting to cancel the noise through differentiation, have added complexity to ambulatory monitoring systems and at best offered only piecemeal solutions.

SUMMARY OF THE INVENTION

The present invention provides dual path noise detection and isolation for an acoustic respiration monitoring system. Dual path noise detection and isolation invokes two discrete techniques to detect noise in an acoustic signal recording lung sounds. A first technique detects portions of the signal that exhibit long-term, moderate amplitude noise by analyzing cumulative energy in the signal. A second technique detects portions of the signal that exhibit short-term, high amplitude noise by analyzing peak energy in the signal. Noisy portions of the signal are isolated using the combined results of the dual path detection. A respiration parameter is estimated using the signal without resort to the noisy portions and information based at least in part on the respiration parameter is outputted.

In one aspect of the invention, a method for processing an acoustic signal comprises the steps of receiving by a respiration monitoring system an acoustic signal recording body sounds; detecting by the system first noisy portions of the signal based at least in part on cumulative energies in the signal; detecting by the system second noisy portions of the signal based at least part on peak energies in the signal; isolating by the system third noisy portions of the signal based at least in part on the first noisy portions and the second noisy portions; calculating by the system a respiration parameter estimate using the signal without resort to the third noisy portions; and outputting by the system information based at least in part on the respiration parameter estimate.

In some embodiments, the first detecting step comprises comparing cumulative energies of portions of the signal with a cumulative energy threshold.

In some embodiments, the cumulative energy threshold is dynamically adjusted based at least in part on cumulative energies of portions of the signal.

In some embodiments, the first detecting step comprises identifying, as first noisy portions, portions of the signal above a cumulative energy threshold.

In some embodiments, the second detecting step comprises comparing peak energies of portions of the signal with a peak energy threshold.

In some embodiments, the second detecting step comprises identifying boundaries of portions of the signal having peak energies above the peak energy threshold at a percentage of the peak energies.

In some embodiments, the second detecting step comprises identifying, as second noisy portions, portions of the signal having peak energies above a peak energy threshold and boundaries at a percentage of the peak energies.

In some embodiments, the isolating step comprises designating, as third noisy portions, intersections between first noisy portions that envelop second noisy portions and second noisy portions that are enveloped by first noisy portions.

In some embodiments, the isolating step comprises designating, as third noisy portions, unions of first noisy portions that do not envelop second noisy portions and second noisy portions that are not enveloped by first noisy portions.

In some embodiments, the method is performed on a portable ambulatory monitoring device.

In another aspect of the invention, a respiration monitoring system comprises a sound capture system adapted to generate an acoustic signal recording body sounds; an acoustic signal processing system adapted to receive from the sound capture system the signal, detect first noisy portions of the signal based at least in part on cumulative energies in the signal, detect second noisy portions of the signal based at least part on peak energies in the signal, isolate third noisy portions of the signal based at least in part on the first noisy portions and the second noisy portions and calculate a respiration parameter estimate using the signal without resort to the third noisy portions; and a respiration data output system adapted to output information based at least in part on the respiration parameter estimate.

These and other aspects of the invention will be better understood by reference to the following detailed description taken in conjunction with the drawings that are briefly described below. Of course, the invention is defined by the appended claims.

DETAILED DESCRIPTION OF A PREFERRED EMBODIMENT

Figure 1:
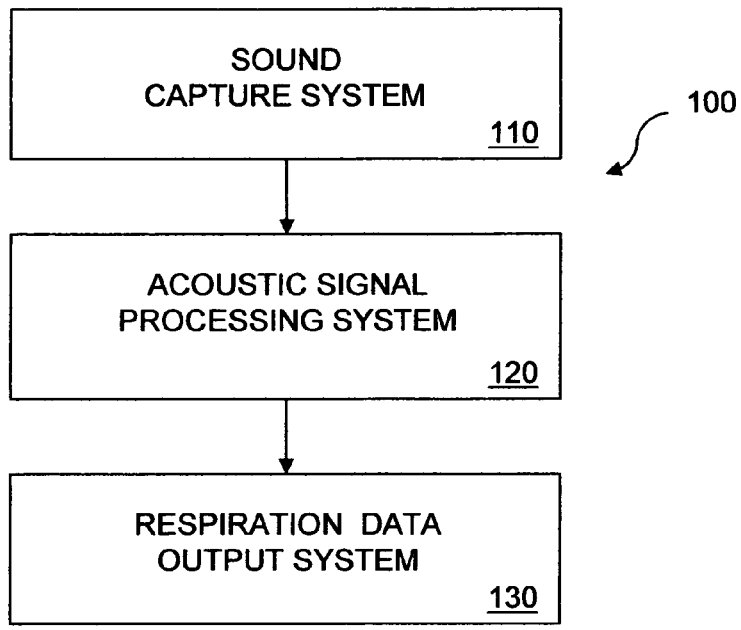
FIG. 1 shows a respiration monitoring system in some embodiments of the invention.

FIG. 1 shows a respiration monitoring device 100 in some embodiments of the invention. Monitoring device 100 includes a sound capture system 110, an acoustic signal processing system 120 and a respiration data output system 130, which are communicatively coupled in series.

Capture system 110 continually detects body sounds, such as heart and lung sounds, at a detection point, such as a trachea, chest or back of a person being monitored, and continually transmits an acoustic signal recording the detected body sounds to processing system 120. Capture system 110 may include, for example, a sound transducer positioned on the body of a human subject that detects body sounds, as well as amplifiers, filters, an analog/digital converter and/or automatic gain control that generate an acoustic signal embodying the detected body sounds.

Processing system 120, under control of a processor executing software instructions, continually processes the acoustic signal and generates estimates of one or more respiration parameters for the subject being monitored. Monitored respiration parameters may include, for example, respiration rate, fractional inspiration time and/or inspiration to expiration time ratio. To enable reliable estimation of respiration parameters, processing system 120 continually evaluates the acoustic signal and detects and isolates noisy portions of the signal, which isolated noisy portions are excluded from the calculation of respiration parameter estimates. Processing system 120 transmits to output system 130 for outputting information relative to calculated respiration parameter estimates. In some embodiments, processing system 120 performs processing operations described herein in custom logic, or in a combination of software and custom logic.

In some embodiments, output system 130 has a display screen for displaying respiration data determined using respiration parameter estimates received from processing system 120. In some embodiments, output system 130 in lieu of or in addition to a display screen has an interface to an internal or external data management system that stores respiration data determined using respiration parameter estimates received from processing system 120 and/or an interface that transmits respiration data determined using respiration parameter estimates received from processing system 120 to a remote monitoring device, such as a monitoring device at a clinician facility. Respiration data outputted by output system 130 may include respiration parameter estimates received from processing system 120 and/or respiration data derived from such respiration parameter estimates.

In some embodiments, capture system 110, processing system 120 and output system 130 are part of a portable ambulatory monitoring device that monitors a person's respiratory health in real-time as the person performs daily activities. In other embodiments, capture system 110, processing system 120 and output system 130 are part of separate devices that are remotely coupled via wired or wireless data communication links.

Figure 2:
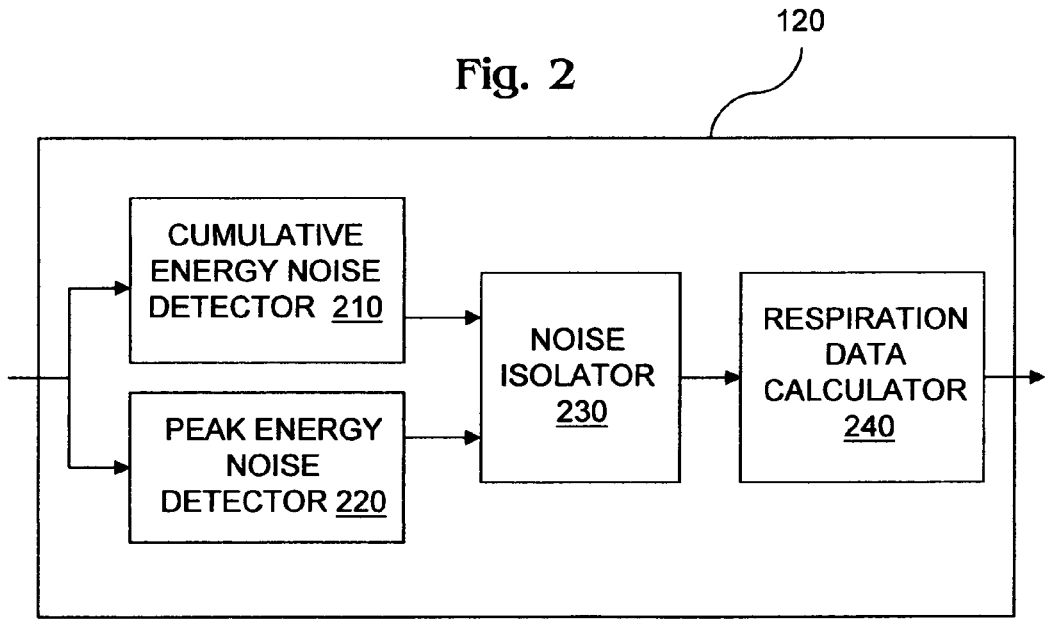
FIG. 2 shows an acoustic signal processing system in some embodiments of the invention.

FIG. 2 shows processing system 120 to include a cumulative energy (CE) noise detector 210 and a peak energy (PE) noise detector 220 operating on separate paths, followed in sequence by a noise isolator 230 and a respiration data calculator 240. As described in FIGS. 3-5 in some embodiments, detectors 210, 220 and isolator 230, under processor control, combine to deliver a dual path noise detection and isolation capability that operates on a raw acoustic signal continually received from capture system 110 to detect and isolate noisy portions of the signal. Calculator 240 calculates respiration parameter estimates using the signal, excluding the isolated noisy portions from the calculation.

Figure 3:
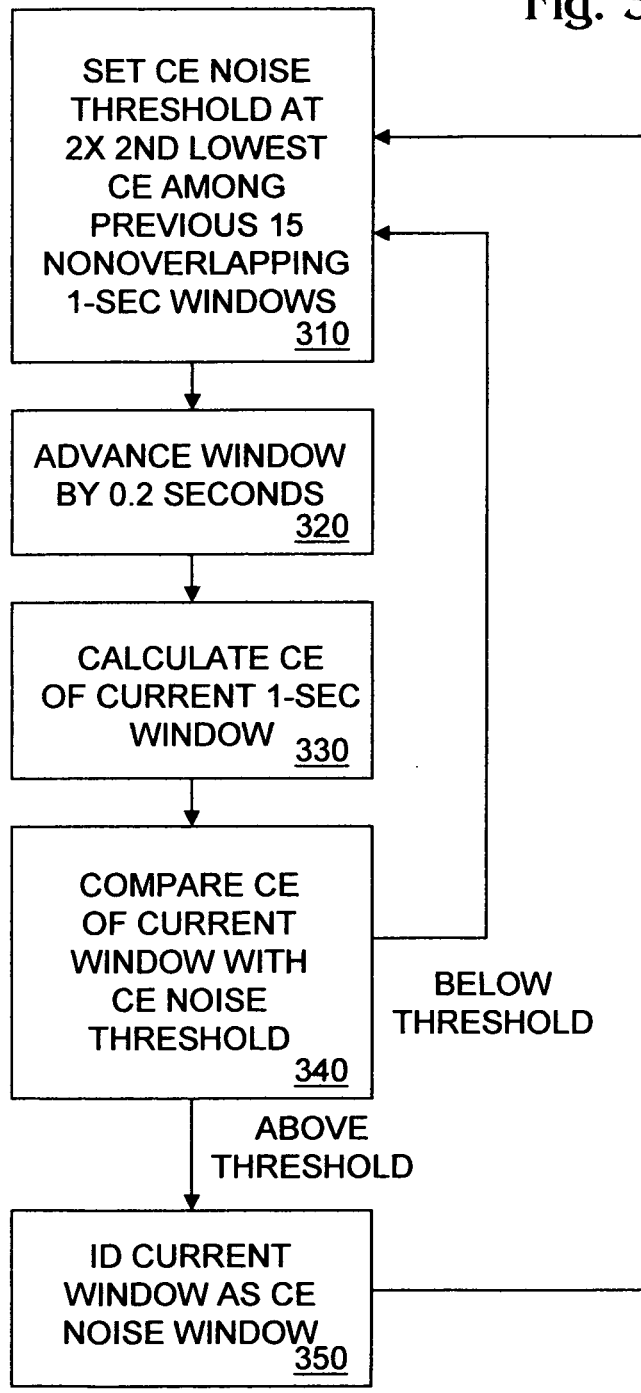
FIG. 3 shows acoustic signal processing steps performed by a cumulative energy noise detector in some embodiments of the invention.
Figure 6A:
FIG. 6A shows the absolute value of a first exemplary acoustic signal segment.
Figure 6B:
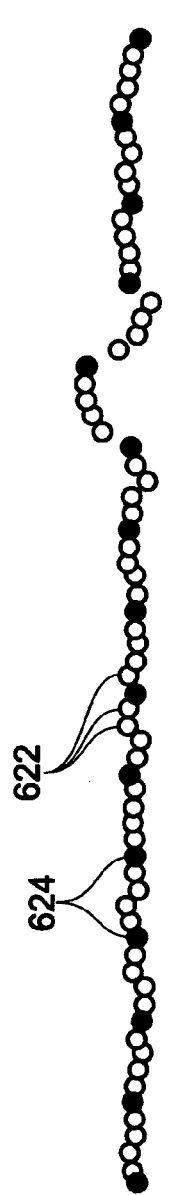
FIG. 6B shows cumulative energy data generated from the first segment.

In runtime operation, a raw acoustic signal is continually fed to CE noise detector 210 and PE noise detector 220 and subjected in parallel to the following steps. Turning first to FIG. 3, at CE noise detector 210, a dynamic CE noise threshold for application to a current one-second window is set at two times the second lowest calculated CE among the fifteen immediately preceding non-overlapping one-second windows (310). Default CEs are used until fifteen windows become available. The current window, which is a sliding window, is then advanced by 0.2 seconds (320). The CE of the current window is then calculated by summing the square of the signal over the current window (325). The CE of the current window is then compared with the CE noise threshold (330). If the CE of the current window is above the CE noise threshold, the current window is identified as a CE noise window (350) and the flow returns to Step 310 where the CE noise threshold is updated and applied to the next window (offset 0.2 seconds from the current window). If, however, the CE of the current window is below the CE noise threshold, the flow returns to Step 310 without identifying the current window as a CE noise window. For example, FIG. 6A shows the absolute value of a first exemplary raw acoustic signal segment received by CE noise detector 210. FIG. 6B shows cumulative energy data generated from the first segment after processing by CE noise detector 210. Each white dot (e.g., 622) represents a CE of a current window calculated by summing the square of the signal over the current window. Each black dot (e.g., 624) represents one of the fifteen non-overlapping CEs used to calculate the CE noise threshold.

Figure 4:
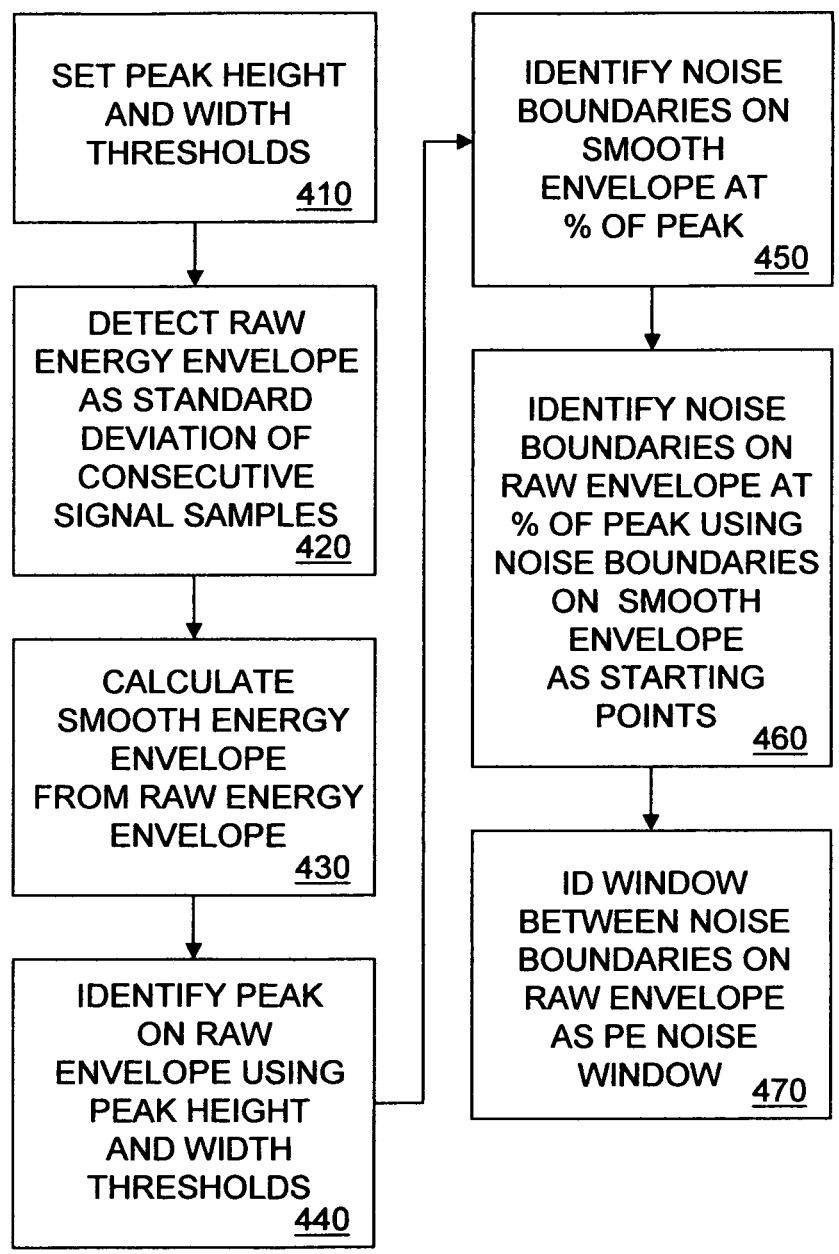
FIG. 4 shows acoustic signal processing steps performed by a peak energy noise detector in some embodiments of the invention.
Figure 5:
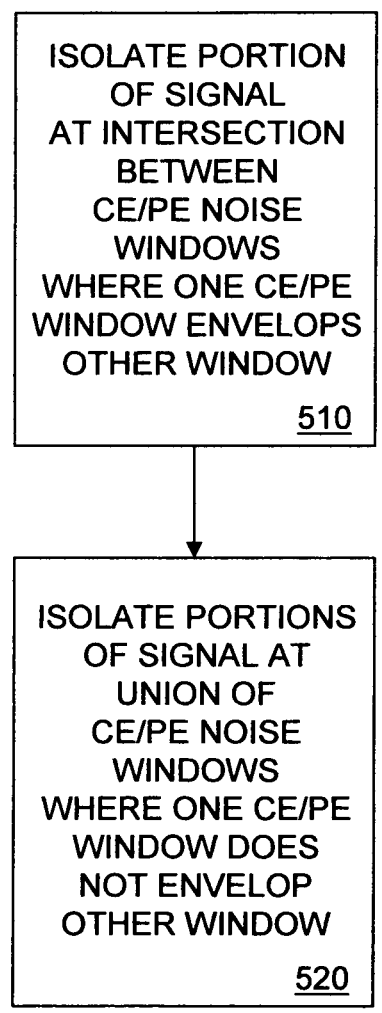
FIG. 5 shows acoustic signal processing steps performed by a noise isolator in some embodiments of the invention.
Figure 6C:
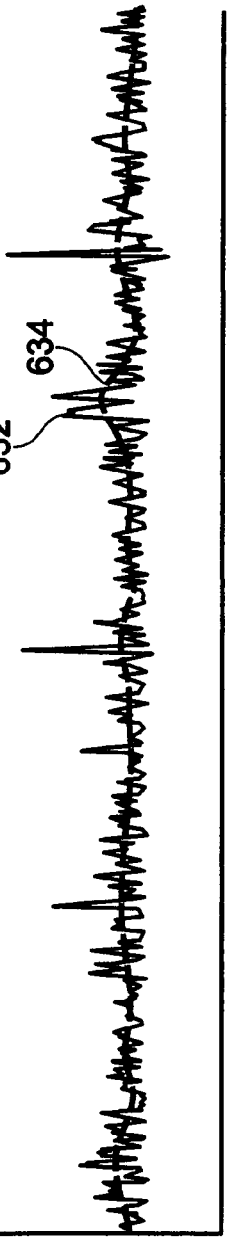
FIG. 6C shows energy envelopes detected from the first segment.

FIG. 4 shows runtime operation at PE noise detector 220. Before runtime operation, peak height and width thresholds are configured (410). When the raw acoustic signal is received, the standard deviation of a certain number of (e.g., 20) consecutive samples of the signal is calculated to detect a raw energy envelope (420). A smooth energy envelope is then generated by applying a smoothing function to the raw energy envelope (430). Peaks that exceed the peak height and width thresholds are then identified on the raw energy envelope (440). Left and right noise boundaries for each peak are then identified as follows: First, as the raw energy envelope may exhibit large fluctuation, preliminary noise boundaries are identified along the smooth energy envelope on the left and right side of the peak at a first percentage of the peak amplitude (450). Final noise boundaries are then identified along the raw energy envelope on the left and right side of the peak by tracing upward along the raw energy envelope starting from the left and right preliminary noise boundaries until a second percentage of the peak amplitude is reached (460). The first and second percentages used in noise boundary identification are configured prior to runtime operation. Finally, the window between the noise boundaries on the raw energy envelope is marked as a PE noise window (470). FIG. 6C shows energy envelopes detected from the first segment after processing by PE noise detector 220. The energy envelopes include a raw energy envelope 632 and smooth energy envelope 634.

After processing by CE noise detector 210 and PE noise detector 220, the acoustic signal is fed to noise isolator 230. Noise isolator 230 designates as final noise windows and isolates the intersection of portions of the signal where a CE noise window envelops a PE noise window and the intersection of portions of the signal where a PE noise window envelops a CE noise window (510). Noise isolator 230 also designates as final windows and isolates the union of portions of the signal where a CE noise window is found that does not envelop a PE noise window and portions of the signal where a PE noise window is found that does not envelop a CE noise window (520).

Figure 7A:
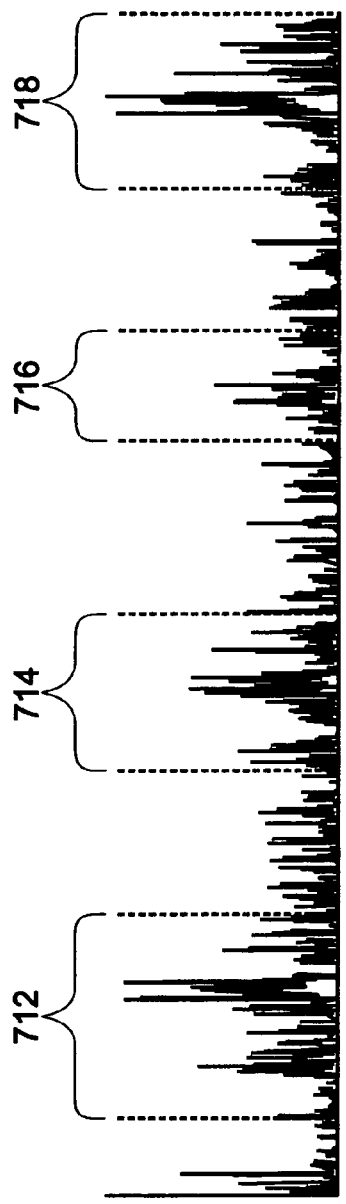
FIG. 7A shows the absolute value of a second exemplary acoustic signal segment, with detected cumulative energy noise windows.
Figure 7B:
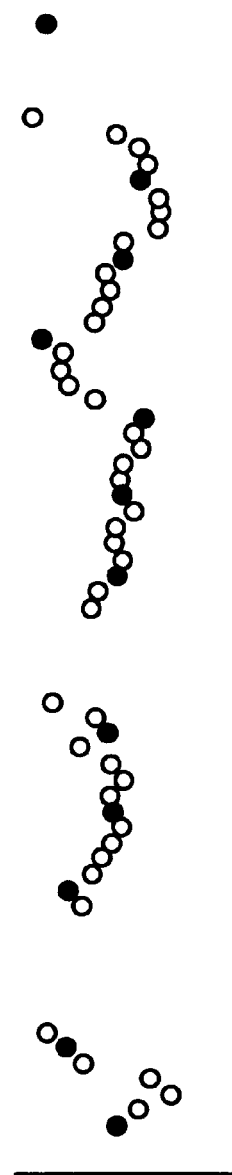
FIG. 7B shows cumulative energy data generated from the second segment.
Figure 7C:
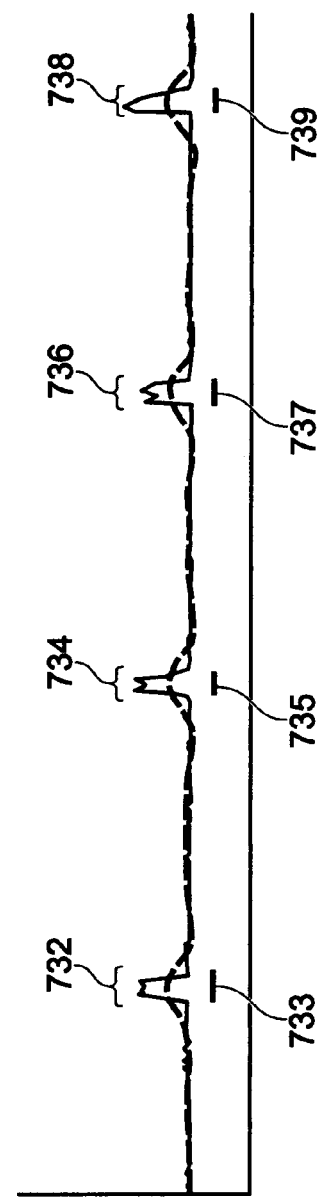
FIG. 7C shows energy envelopes detected from the second segment, with detected peak energy noise windows and isolated portions of the segment.

FIGS. 7A-7C illustrate processing of a second exemplary acoustic signal segment by detectors 210, 220 and isolator 230. FIG. 7A shows the absolute value of the raw segment as received by CE noise detector 210 and PE noise detector 220. FIG. 7B shows cumulative energy data generated from the segment after processing by CE noise detector 210. CE noise windows 712, 714, 716, 718 detected as a result of such processing are identified in FIG. 7A. FIG. 7C shows energy envelopes detected from the segment after processing by PE noise detector 220. PE noise windows 732, 734, 736, 738 detected as a result of such processing are identified in FIG. 7C. Since CE noise windows 712, 714, 716, 718 envelop PE noise windows 732, 734, 736, 738, respectively, noise isolator 230 designates as final noise windows 733, 735, 737, 739 the intersection between CE noise windows 712, 714, 716, 718 and PE noise windows 732, 734, 736, 738 and isolates final noise windows 732, 734, 736, 738.

Figure 8A:
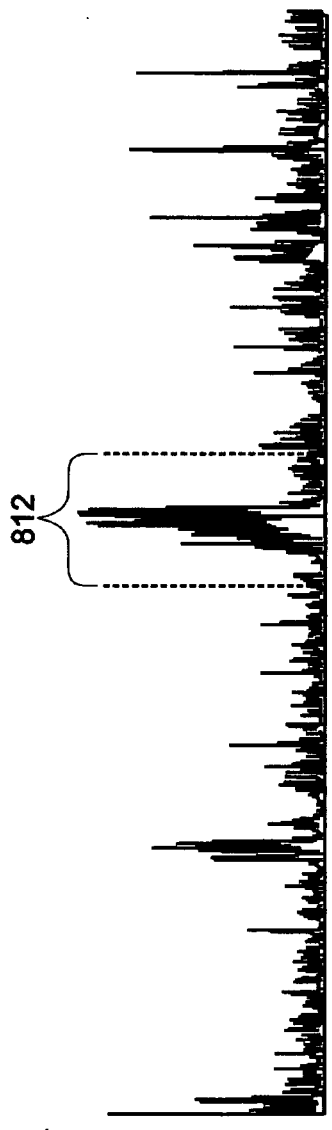
FIG. 8A shows the absolute value of a third exemplary acoustic signal segment, with detected cumulative energy noise windows.
Figure 8B:
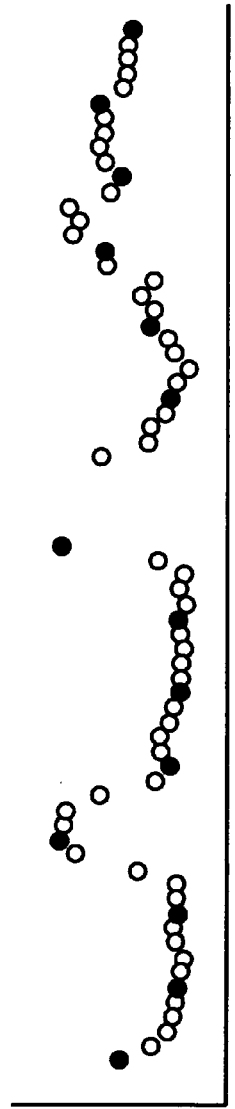
FIG. 8B shows cumulative energy data generated from the third segment.
Figure 8C:
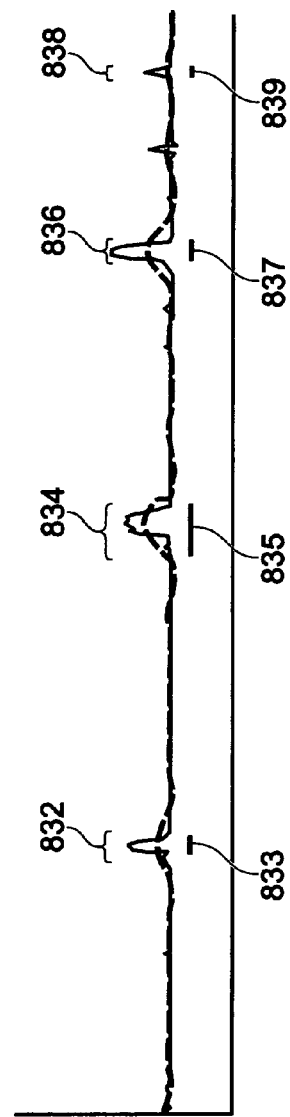
FIG. 8C shows energy envelopes detected from the third segment, with detected peak energy noise windows and isolated portions of the segment.

FIGS. 8A-8C illustrate processing of a third exemplary acoustic signal segment by detectors 210, 220 and isolator 230. FIG. 7A shows the absolute value of the raw segment as received by CE noise detector 210 and PE noise detector 220. FIG. 7B shows cumulative energy data generated from the segment after processing by CE noise detector 210. CE noise window 812 is detected as a result of such processing and identified in FIG. 8A. FIG. 8C shows energy envelopes detected from the segment after processing by PE noise detector 220. PE noise windows 832, 834, 836, 838 detected as a result of such processing are identified in FIG. 8C. Since CE noise window 812 envelops PE noise window 834, noise isolator 230 designates as a final noise window 835 the intersection between CE noise window 812 and PE noise window 834. However, since other PE noise windows 832, 836, 838 are not enveloped by any CE noise window and do not envelop any CE noise window, noise isolator 230 designates the union of these windows 832, 836, 838 as final noise windows 833, 837, 839. Noise isolator 230 isolates final noise windows 833, 835, 837, 839.

After processing by noise isolator 230, the acoustic signal is fed to calculator 240. Calculator 240 calculates estimates of one or more respiration parameters using portions of the signal that have not been isolated. Calculator 240 excludes from use in the calculations portions of the signal that have been isolated. Calculator 240 transmits the estimates to output system 130, which outputs respiration data that may include the estimates themselves and/or respiration data derived from the estimates.

It will be appreciated by those of ordinary skill in the art that the invention can be embodied in other specific forms without departing from the spirit or essential character hereof. For example, before respiration parameter estimates are calculated, the acoustic signal may be processed using filters to remove unwanted (e.g., non-respiration) signal components, such as heart sounds. Moreover, the acoustic signal may be processed to isolate and distinguish respiration phases (e.g., inspiration and expiration) and silent phases in the signal. The present description is thus considered in all respects to be illustrative and not restrictive. The scope of the invention is indicated by the appended claims, and all changes that come within the meaning and range of equivalents thereof are intended to be embraced therein.

What is claimed is:

1. A method for processing an acoustic signal, comprising the steps of:
   receiving an acoustic signal recording body sounds on a respiration monitoring system;
   detecting first noisy portions of the signal based at least in part on cumulative energies in the signal with the system;
   detecting second noisy portions of the signal based at least part on peak energies in the signal with the system;
   isolating third noisy portions of the signal based at least in part on the first noisy portions and the second noisy portions with the system, including designating, as third noisy portions, intersections between first noisy portions that envelop second noisy portions and second noisy portions that are enveloped by first noisy portions;

calculating a respiration parameter estimate using the signal without resort to the third noisy portions with the system; and outputting information based at least in part on the respiration parameter estimate on the system.

2. The method of claim 1, wherein the first detecting step comprises comparing cumulative energies of portions of the signal with a cumulative energy threshold.

3. The method of claim 2, wherein the cumulative energy threshold is dynamically adjusted based at least in part on cumulative energies of portions of the signal.

4. The method of claim 1, wherein the first detecting step comprises identifying, as first noisy portions, portions of the signal above a cumulative energy threshold.

5. The method of claim 1, wherein the second detecting step comprises comparing peak energies of portions of the signal with a peak energy threshold.

6. The method of claim 1, wherein the second detecting step comprises identifying boundaries of portions of the signal having peak energies above the peak energy threshold at a percentage of the peak energies.

7. The method of claim 1, wherein the second detecting step comprises identifying, as second noisy portions, portions of the signal having peak energies above a peak energy threshold and boundaries at a percentage of the peak energies.

8. The method of claim 1, wherein the isolating step further comprises designating, as third noisy portions, unions of first noisy portions that do not envelop second noisy portions and second noisy portions that are not enveloped by first noisy portions.

9. The method of claim 1, wherein the method is performed on a portable ambulatory monitoring device.

10. A respiration monitoring system, comprising:
a sound capture system adapted to generate an acoustic signal recording body sounds;
an acoustic signal processing system adapted to receive from the sound capture system the signal, detect first noisy portions of the signal based at least in part on cumulative energies in the signal, detect second noisy portions of the signal based at least part on peak energies in the signal, isolate third noisy portions of the signal based at least in part on the first noisy portions and the second noisy portions, including designating, as third noisy portions, intersections between first noisy portions that envelop second noisy portions and second noisy portions that are enveloped by first noisy portions, and calculate a respiration parameter estimate using the signal without resort to the third noisy portions; and
a respiration data output system adapted to output information based at least in part on the respiration parameter estimate.

11. The monitoring system of claim 10, wherein the processing system is adapted to compare cumulative energies of portions of the signal with a cumulative energy threshold.

12. The monitoring system of claim 11, wherein the processing system is adapted to dynamically adjust the cumulative energy threshold based at least in part on cumulative energies of portions of the signal.

13. The monitoring system of claim 10, wherein the processing system is adapted to identify, as first noisy portions, portions of the signal above a cumulative energy threshold.

14. The monitoring system of claim 10, wherein the processing system is adapted to compare peak energies of portions of the signal with a peak energy threshold.

15. The monitoring system of claim 10, wherein the processing system is adapted to identify boundaries of portions of the signal having peak energies above the peak energy threshold at a percentage of the peak energies.

16. The monitoring system of claim 10, wherein the processing system is adapted to identify, as second noisy portions, portions of the signal having peak energies above a peak energy threshold and boundaries at a percentage of the peak energies.

17. The monitoring system of claim 10, wherein the processing system is further adapted to designate, as third noisy portions, unions of first noisy portions that do not envelop second noisy portions and second noisy portions that are not enveloped by first noisy portions.

18. The monitoring system of claim 10, wherein the monitoring system is a portable ambulatory monitoring device.

19. A method for processing an acoustic signal, comprising the steps of:
receiving an acoustic signal recording body sounds on a respiration monitoring system;
detecting first noisy portions of the signal based at least in part on cumulative energies in the signal with the system;
detecting second noisy portions of the signal based at least part on peak energies in the signal with the system;
isolating third noisy portions of the signal based at least in part on the first noisy portions and the second noisy portions with the system, including designating, as third noisy portions, unions of first noisy portions that do not envelop second noisy portions and second noisy portions that are not enveloped by first noisy portions;
calculating a respiration parameter estimate using the signal without resort to the third noisy portions with the system; and
outputting information based at least in part on the respiration parameter estimate on the system.

20. A respiration monitoring system, comprising:
a sound capture system adapted to generate an acoustic signal recording body sounds;
an acoustic signal processing system adapted to receive from the sound capture system the signal, detect first noisy portions of the signal based at least in part on cumulative energies in the signal, detect second noisy portions of the signal based at least part on peak energies in the signal, isolate third noisy portions of the signal based at least in part on the first noisy portions and the second noisy portions, including designating, as third noisy portions, unions of first noisy portions that do not envelop second noisy portions and second noisy portions that are not enveloped by first noisy portions, and calculate a respiration parameter estimate using the signal without resort to the third noisy portions; and
a respiration data output system adapted to output information based at least in part on the respiration parameter estimate.

* * * * *